(12) United States Patent
Gailey et al.

(10) Patent No.: US 11,938,064 B2
(45) Date of Patent: Mar. 26, 2024

(54) MOBILE OXYGEN POINT OF USE APPARATUS

(71) Applicant: Lincoln Global, Inc., Santa Fe Springs, CA (US)

(72) Inventors: David W. Gailey, Lula, GA (US); Thomas S. Trame, Jr., Cincinnati, OH (US)

(73) Assignee: LINCOLN GLOBAL, INC., Santa Fe Springs, CA (US)

( * ) Notice: Subject to any disclaimer, the term of this patent is extended or adjusted under 35 U.S.C. 154(b) by 464 days.

(21) Appl. No.: 17/227,437

(22) Filed: Apr. 12, 2021

(65) Prior Publication Data

US 2022/0015974 A1  Jan. 20, 2022

Related U.S. Application Data

(60) Provisional application No. 63/052,516, filed on Jul. 16, 2020.

(51) Int. Cl.
*A61G 12/00* (2006.01)
*A61M 16/00* (2006.01)
(Continued)

(52) U.S. Cl.
CPC ......... *A61G 12/008* (2013.01); *A61G 12/007* (2013.01); *A61M 16/0816* (2013.01);
(Continued)

(58) Field of Classification Search
CPC .............. A61M 16/00; A61M 16/0057; A61M 16/0816; A61M 16/0875; A61M 16/10;
(Continued)

(56) References Cited

U.S. PATENT DOCUMENTS 2,490,839 A * 12/1949 Shaffer' .................... B23K 5/22
239/722
4,413,622 A * 11/1983 Austin ...................... A62B 7/00
128/202.13
(Continued)

FOREIGN PATENT DOCUMENTS

AU           767181 B2 *  8/2001   ............. A62B 11/00
CN       208997704 U  *  6/2019   ............... F17C 7/00
(Continued)

OTHER PUBLICATIONS

Oxford English Dictionary definition of "panel"; retrieved from https://www.oed.com/dictionary/panel_n1.*
(Continued)

*Primary Examiner* — Joseph D. Boecker
(74) *Attorney, Agent, or Firm* — David J. Muzilla

(57) ABSTRACT

A mobile oxygen point of use apparatus includes a stand-alone and portable mounting panel having a first side and a second side and is configured to be portably relocated within a facility by at least one human operator. A first set of oxygen flow regulators are mounted on the first side of the mounting panel and have multiple first oxygen inputs and multiple first oxygen outputs. A second set of oxygen flow regulators are mounted on the second side of the mounting panel and have multiple second oxygen inputs and multiple second oxygen outputs. A low pressure oxygen input is mounted on the mounting panel and a single pipeline or hose is configured to be connected from the low pressure oxygen input to a source of oxygen. Distribution plumbing connects the low pressure oxygen input to the multiple first oxygen inputs and the multiple second oxygen inputs.

16 Claims, 7 Drawing Sheets

(51) Int. Cl.
*A61M 16/06* (2006.01)
*A61M 16/08* (2006.01)
*A61M 16/10* (2006.01)
*A61M 16/16* (2006.01)
*A61M 16/20* (2006.01)

(52) U.S. Cl.
CPC ............ *A61M 16/10* (2013.01); *A61M 16/20* (2013.01); *A61M 16/00* (2013.01); *A61M 16/0672* (2014.02); *A61M 16/0875* (2013.01); *A61M 16/16* (2013.01); *A61M 2202/0208* (2013.01); *A61M 2205/3331* (2013.01); *A61M 2205/84* (2013.01); *A61M 2209/084* (2013.01)

(58) Field of Classification Search
CPC .............. A61M 16/1005; A61M 16/20; A61M 2202/0208; A61M 2205/84; A61M 2209/084; A61G 12/007; A61G 12/008; A61G 10/04; A62B 7/02; A62B 7/14; A62B 13/00; A62B 29/00; A62B 31/00; B64D 2013/0677; B64D 2231/02
See application file for complete search history.

(56) References Cited

U.S. PATENT DOCUMENTS

| | | | |
|---|---|---|---|
| 5,644,876 A | 7/1997 | Walker | |
| 6,305,400 B1 | 10/2001 | Simo et al. | |
| 6,948,493 B2 | 9/2005 | Dunlop | |
| 7,819,118 B2 | 10/2010 | Lucas, Jr. et al. | |
| 8,640,391 B2 | 2/2014 | Newkirk et al. | |
| 9,237,979 B2 | 1/2016 | Carnell et al. | |
| 2002/0104271 A1 | 8/2002 | Gallant | |
| 2008/0011299 A1* | 1/2008 | Lucas | A61M 16/10 128/205.24 |
| 2010/0052351 A1* | 3/2010 | Sartin | A61G 3/067 296/20 |
| 2012/0258655 A1* | 10/2012 | Carnell | E04H 3/08 454/284 |
| 2019/0269868 A1* | 9/2019 | McBride | A61M 16/0816 |
| 2020/0215358 A1* | 7/2020 | Degenhardt | A62B 7/04 |
| 2021/0346638 A1* | 11/2021 | Faulkner | A61M 16/024 |

FOREIGN PATENT DOCUMENTS

| | | |
|---|---|---|
| WO | 89/07357 A1 | 8/1989 |
| WO | 2019/178556 A1 | 9/2019 |

OTHER PUBLICATIONS

Western Medica, "Portable Emergency O2 Manifold" discussing Octi-FLO2™; retrieved from https://cdn.boundtree.com/btm/other/Bound_Tree_Octi-flo_product_flyer_8909542948894.pdf (Year: 2008).*

Sampson; "Coronavirus: Air Liquide providing oxygen to field hospitals in Brazil;" https://www.gasworld.com/air-liquide-providing-oxygen-to-field-hospitals-in-brazil/2018859.article; Dated Apr. 15, 2020; pp. 1-2.

PCI Oxygen Solutions; "Disaster Preparedness and Relief Applications Concerning COVID-19;" https://www.pcigases.com/oxygen-solutions/medical-oxygen-generator/disaster-preparedness/; Accessed on Jun. 12, 2020; pp. 1-3.

* cited by examiner

MOBILE OXYGEN POINT OF USE APPARATUS

CROSS REFERENCE TO RELATED APPLICATIONS/INCORPORATION BY REFERENCE

This U.S. patent application claims priority to and the benefit of U.S. Provisional Patent Application Ser. No. 63/052,516 filed on Jul. 16, 2020, which is incorporated herein by reference in its entirety.

FIELD

Embodiments of the present invention relate to oxygen panels. More specifically, embodiments of the present invention relate to mobile oxygen point of use panels.

BACKGROUND

Field hospitals being set up as overflow facilities for local hospitals require oxygen gas to be supplied to each patient bed. The oxygen source may be of several types including bulk, microbulk, liquid dewars, or high pressure cylinders. Such facilities do not normally have gas distribution systems and the challenge is to provide equipment or a gas system that will deliver oxygen gas to various areas within the facility without having to handle individual gas cylinders. Having to handle individual gas cylinders would be too cumbersome and require multiple change outs daily.

SUMMARY

One embodiment of the present invention is a mobile oxygen point of use apparatus that includes a standalone and portable mounting panel having a first side and a second side and is configured to be portably relocated within a facility by at least one human operator. A first set of oxygen flow regulators are mounted on the first side of the mounting panel and have multiple first oxygen inputs and multiple first oxygen outputs. A second set of oxygen flow regulators are mounted on the second side of the mounting panel and have multiple second oxygen inputs and multiple second oxygen outputs. A low pressure oxygen input is mounted on the mounting panel and a single pipeline or hose is configured to be connected from the low pressure oxygen input to a source of oxygen. Distribution plumbing connects the low pressure oxygen input to the multiple first oxygen inputs and the multiple second oxygen inputs. The mobile oxygen point of use apparatus can be located inside a facility, near hospital beds, and can deliver a precise and adjustable dosage of oxygen to multiple patients per panel. A low pressure (e.g., 500 psi or less) or high pressure (e.g., greater than 500 psi) oxygen input is supplied from an oxygen supply upstream and is connected to the panel via a single pipeline or hose. In one embodiment, the mobile oxygen point of use apparatus includes a frame and/or a stand connected to the mounting panel. The frame or the stand is configured to support multiple oxygen tanks as the source of oxygen. The frame or stand includes feet having wheels, casters, or rollers connected to the feet. In one embodiment, the first set of oxygen flow regulators and the second set of oxygen flow regulators are Food and Drug Administration (FDA) Class 1 medical devices. For example, in one embodiment the first set of oxygen flow regulators and the second set of oxygen flow regulators are 15 liters per minute (LPM) Class 1 regulators for use with cannulas or breathing masks. In another embodiment, the first set of oxygen flow regulators and the second set of oxygen flow regulators are 50 pounds per square inch (PSI) preset Class 1 regulators for use with respirators and ventilators.

One embodiment of the present invention is an oxygen distribution system including an embodiment of the mobile oxygen point of use apparatus described herein. The oxygen distribution system also includes a source of oxygen configured to supply oxygen for use by the mobile oxygen point of use apparatus. The source of oxygen may include, for example, a bulk tank oxygen storage system, a microbulk oxygen storage system, a liquid oxygen dewar storage system, or a high pressure cylinder oxygen storage system. In one embodiment, the oxygen distribution system includes a vaporizer configured between the source of oxygen and the mobile oxygen point of use apparatus to add moisture to the oxygen. In one embodiment, the oxygen distribution system includes a bulk manifold having multiple oxygen outputs and being configured between the source of oxygen and multiple mobile oxygen point of use apparatuses. In one embodiment, the source of oxygen includes multiple oxygen tanks, and the mobile oxygen point of use apparatus includes a frame or a stand configured to support the multiple oxygen tanks. In one embodiment, the first set of oxygen flow regulators and the second set of oxygen flow regulators of the mobile oxygen point of use apparatus are 15 LPM Class 1 regulators for use with cannulas or breathing masks. In another embodiment, the first set of oxygen flow regulators and the second set of oxygen flow regulators of the mobile oxygen point of use apparatus are 50 PSI preset Class 1 regulators for use with respirators and ventilators.

Numerous aspects of the general inventive concepts will become readily apparent from the following detailed description of exemplary embodiments, from the claims, and from the accompanying drawings.

BRIEF DESCRIPTION OF THE DRAWINGS

The accompanying drawings, which are incorporated in and constitute a part of the specification, illustrate various embodiments of the disclosure. It will be appreciated that the illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Embodiments of the present invention may include custom and/or off-the-shelf components such as flow regulators, plumbing, and various other hardware mounted to a portable panel. A unique configuration allows oxygen, which is normally piped into a hospital room through a gas distribution system within a wall, to become mobile via a standalone system that can deliver oxygen to multiple patients. The panel can be moved to a strategic location within a facility to allow for the delivery of oxygen to patients at a convenient spot.

Figure 1:
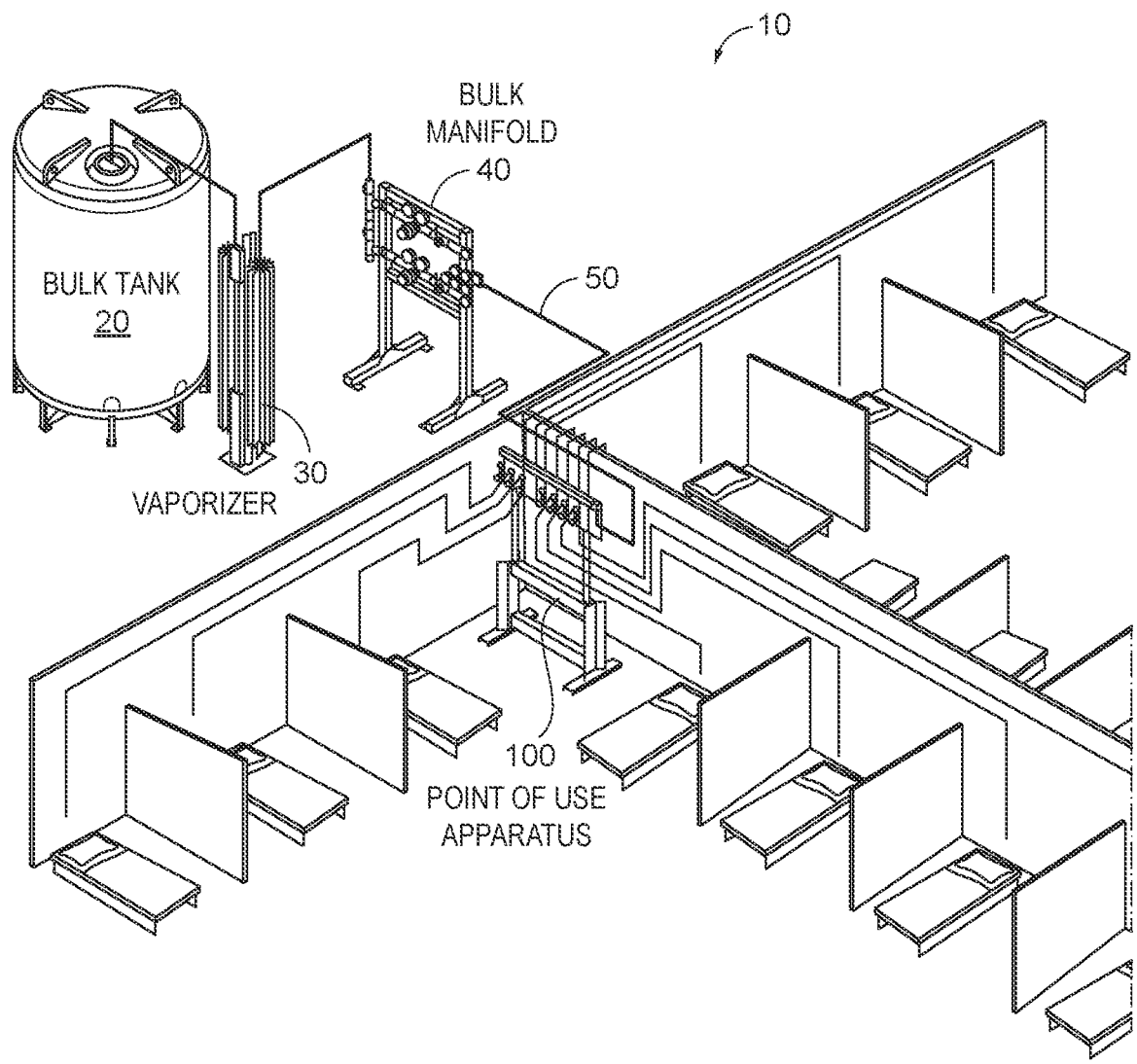
FIG. 1 illustrates one embodiment of an oxygen distribution system, having a mobile oxygen point of use apparatus, set within a field hospital environment.

The examples and figures herein are illustrative only and are not meant to limit the subject invention, which is measured by the scope and spirit of the claims. Referring now to the drawings, wherein the showings are for the purpose of illustrating exemplary embodiments of the subject invention only and not for the purpose of limiting same, FIG. 1 illustrates one embodiment of an oxygen distribution system 10, having a mobile oxygen point of use apparatus 100, set within a field hospital environment. The field hospital environment may include temporary walls and beds or cots, for example.

Referring to FIG. 1, one embodiment of the oxygen distribution system 10 includes a bulk tank 20 of oxygen, a vaporizer 30, a bulk manifold 40, and the mobile oxygen point of use apparatus 100. An output of the bulk tank 20 connects to an input of the vaporizer 30 to add moisture to the oxygen. An output of the vaporizer 30 connects to an input of the bulk manifold 40. In one embodiment, the bulk manifold 40 is configured to provide multiple outputs such that each output of the bulk manifold 40 can provide vaporized oxygen to a single mobile oxygen point of use apparatus. As shown in FIG. 1, one output of the bulk manifold 40 provides vaporized oxygen to an input of the mobile oxygen point of use apparatus 100. In one embodiment, the vaporizer 30 generates water vapor from liquid water, and the oxygen gas from the bulk tank 20 passes through the vaporizer and combines with the water vapor. Efficient vaporization of the oxygen is based on the temperature of the oxygen, the pressure and the temperature of the vaporizer, and the flow rate.

In one alternative embodiment, the vaporizer 30 is not present and the bulk tank 20 connects directly to the bulk manifold 40. In another alternative embodiment, the bulk manifold 40 is not present and the vaporizer 30 connects directly to the mobile oxygen point of use apparatus 100. In yet a further alternative embodiment, the vaporizer 30 and the bulk manifold 40 are not present and the bulk tank 20 connects directly to the mobile oxygen point of use apparatus 100. The mobile oxygen point of use apparatus 100 has multiple outputs to provide oxygen to multiple patients in multiple beds within the environment (e.g., a field hospital environment).

Figure 2:
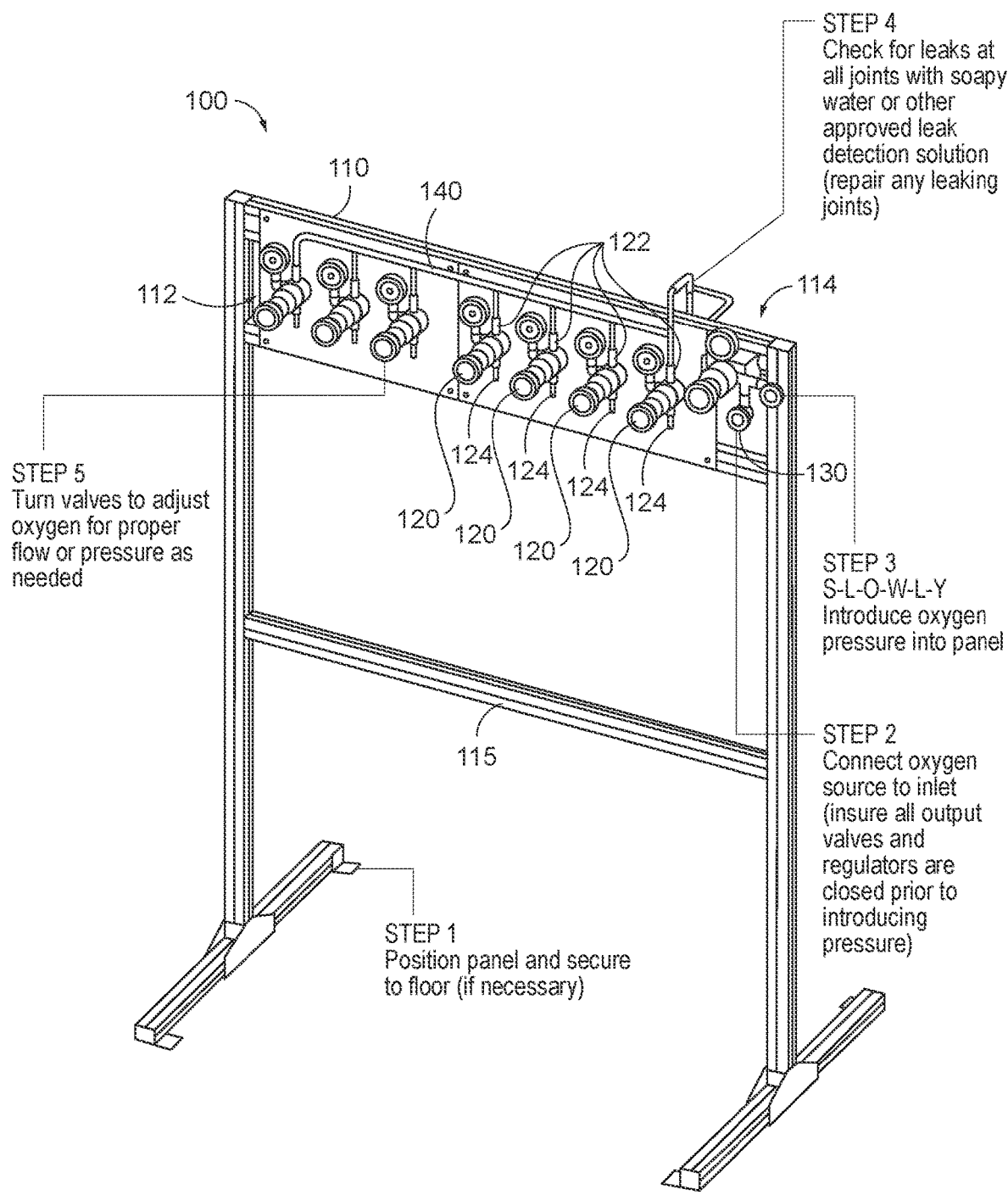
FIG. 2 illustrates one embodiment of the mobile oxygen point of use apparatus of the system of FIG. 1.

FIG. 2 illustrates one embodiment of the mobile oxygen point of use apparatus 100 of the system 10 of FIG. 1. The mobile oxygen point of use apparatus 100 can be located inside a facility, near hospital beds, and can deliver a precise and adjustable dosage of oxygen to multiple patients per panel. The facility may be, for example, a conventional hospital or a field hospital. A low pressure oxygen input is supplied from an oxygen supply upstream and is connected to the panel via a single pipeline or hose. The oxygen supply may include, for example, a bulk tank oxygen storage system, a microbulk oxygen storage system, a liquid oxygen dewar storage system, or a high pressure cylinder oxygen storage system.

The mobile oxygen point of use apparatus 100 includes a standalone and portable mounting panel 110 having a first side 112 and a second side 114 and is configured to be portably relocated within a facility by at least one human operator. The apparatus 100 includes a frame or stand 115 to which the panel 110 is connected. A first set of oxygen flow regulators 120 are mounted on the first side 112 of the mounting panel 110 and have multiple first oxygen inputs 122 and multiple first oxygen outputs 124. Similarly, a second set of oxygen flow regulators 120 (not seen in the view of FIG. 2) are mounted on the second side 114 of the mounting panel 110 and have multiple second oxygen inputs 122 and multiple second oxygen outputs 124. In accordance with one embodiment, the oxygen flow regulators regulate both pressure and flow of the oxygen.

Figure 3:
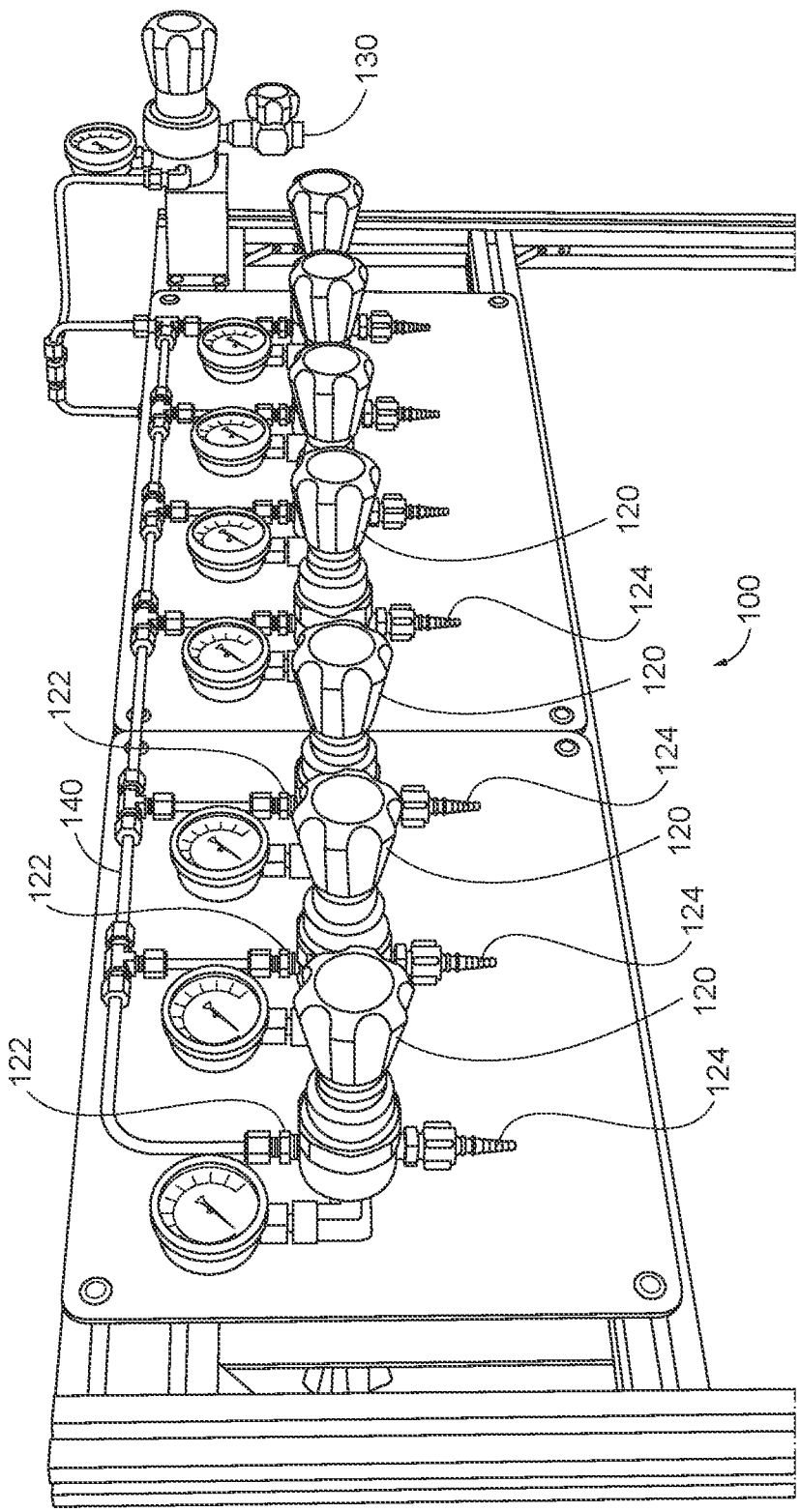
FIG. 3 illustrates a first view of an embodiment of a panel of the mobile oxygen point of use apparatus of FIG. 2.
Figure 4:
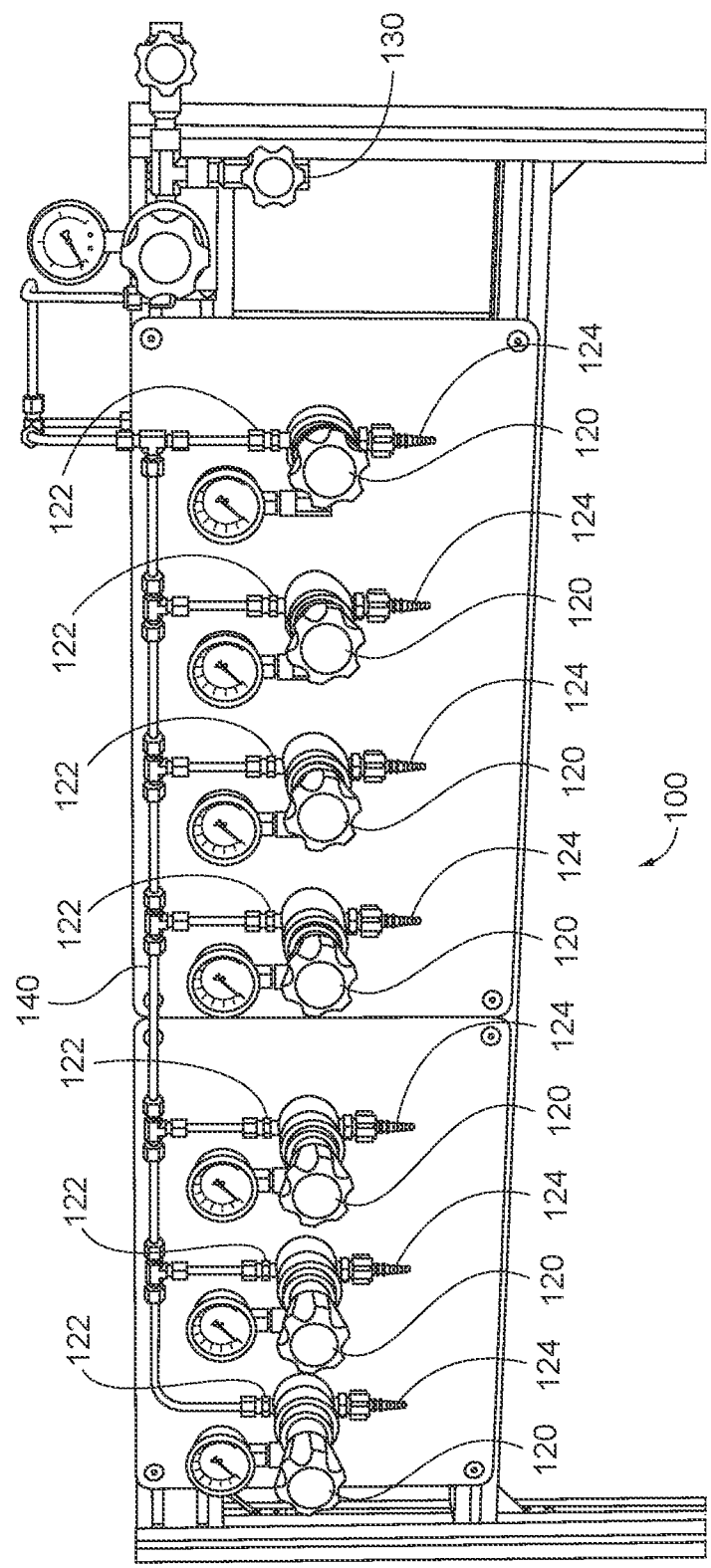
FIG. 4 illustrates a second view of an embodiment of a panel of the mobile oxygen point of use apparatus of FIG. 2.

A low pressure oxygen input 130 is mounted on the mounting panel and a single pipeline or hose 50 (see FIG. 1) is configured to be connected from the low pressure oxygen input 130 to a source of oxygen (e.g., the bulk manifold 40 in FIG. 1). Distribution plumbing 140 connects the low pressure oxygen input 130 to the multiple first oxygen inputs 122 and the multiple second oxygen inputs 122. FIG. 3 illustrates a first view of an embodiment of the panel 110 of the mobile oxygen point of use apparatus 100 of FIG. 2. FIG. 4 illustrates a second view of an embodiment of the panel 110 of the mobile oxygen point of use apparatus 100 of FIG. 2.

Referring again to FIG. 2, a method of setting up and using the mobile oxygen point of use apparatus 100 is now described. In STEP 1, the panel 110 is positioned within the environment and, if necessary, is secured to the floor via the feet of the stand 115 (e.g., via screws or other securing means). In another embodiment, the feet of the stand 115 may include wheels, casters, or rollers to allow easy movement of the apparatus 100. In STEP 2, an oxygen source (e.g., the bulk manifold 40) is connected to the low pressure oxygen input 130. All output valves and regulators are to be closed prior to introducing pressure. In STEP 3, oxygen pressure is slowly introduced into the panel 110. In STEP 4, leaks are checked for at all plumbing joints using, for example, soapy water or another approved leak detection solution. Any discovered leaks are to be repaired. In STEP 5, valves of the regulators 120 are turned to adjust oxygen for proper flow or pressure as needed. In accordance with one embodiment, the regulators 120 are configured to be adjusted for both pressure and flow.

Figure 5:
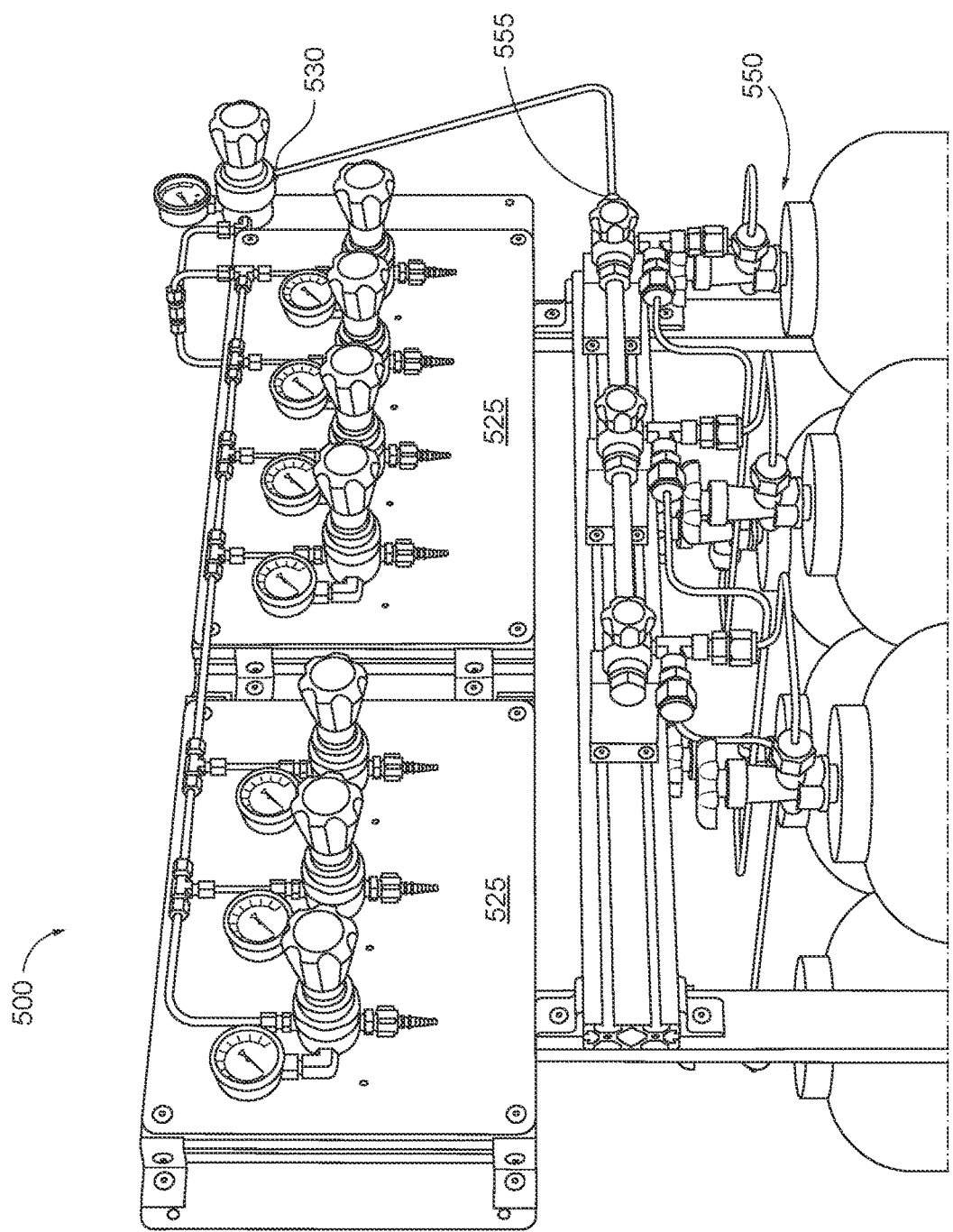
FIG. 5 illustrates an embodiment of an alternate mobile oxygen point of use apparatus connected to a local source of oxygen.

FIG. 5 illustrates an embodiment of an alternate mobile oxygen point of use apparatus 500 connected to a source of oxygen 550 which is local to the apparatus 500. The apparatus 500 is similar to the apparatus 100 herein. However, the apparatus 500 is configured to support multiple oxygen tanks (the source of oxygen 550) beneath a panel 525 of the apparatus 500. The outputs of the multiple oxygen tanks are connected together and a single output 555 of the source of oxygen 550 is provided which connects to a low pressure oxygen input 530 of the panel 525.

In one embodiment, a mobile oxygen point of use apparatus uses existing Food and Drug Administration (FDA) Class 1 medical devices (flow regulators). The regulators are reconfigured to be mounted onto a panel such that oxygen from each regulator can be directed to a separate patient. The apparatus can use either 0-15 liters per minute (LPM) Class 1 regulators for nasal cannulas or breathing masks, or 0-50 pounds per square inch (PSI) preset Class 1 regulators for respirators and ventilators. In general, a Class 1 medical device has a low to moderate risk to the user. Many Class 1 medical devices are not subject to the regulatory process. A nasal cannula is configured to provide oxygen/air to a user via a lightweight tube having two prongs that are positioned in the nostrils of the user. A breathing mask is configured to fit over the nose and mouth of the user and provide oxygen/air to a user via a tube attached to the mask. A respirator or ventilator is configured to provide mechanical ventilation by moving oxygen/air in and out of the lungs of a user via a mask and/or a breathing tube.

Figure 6:
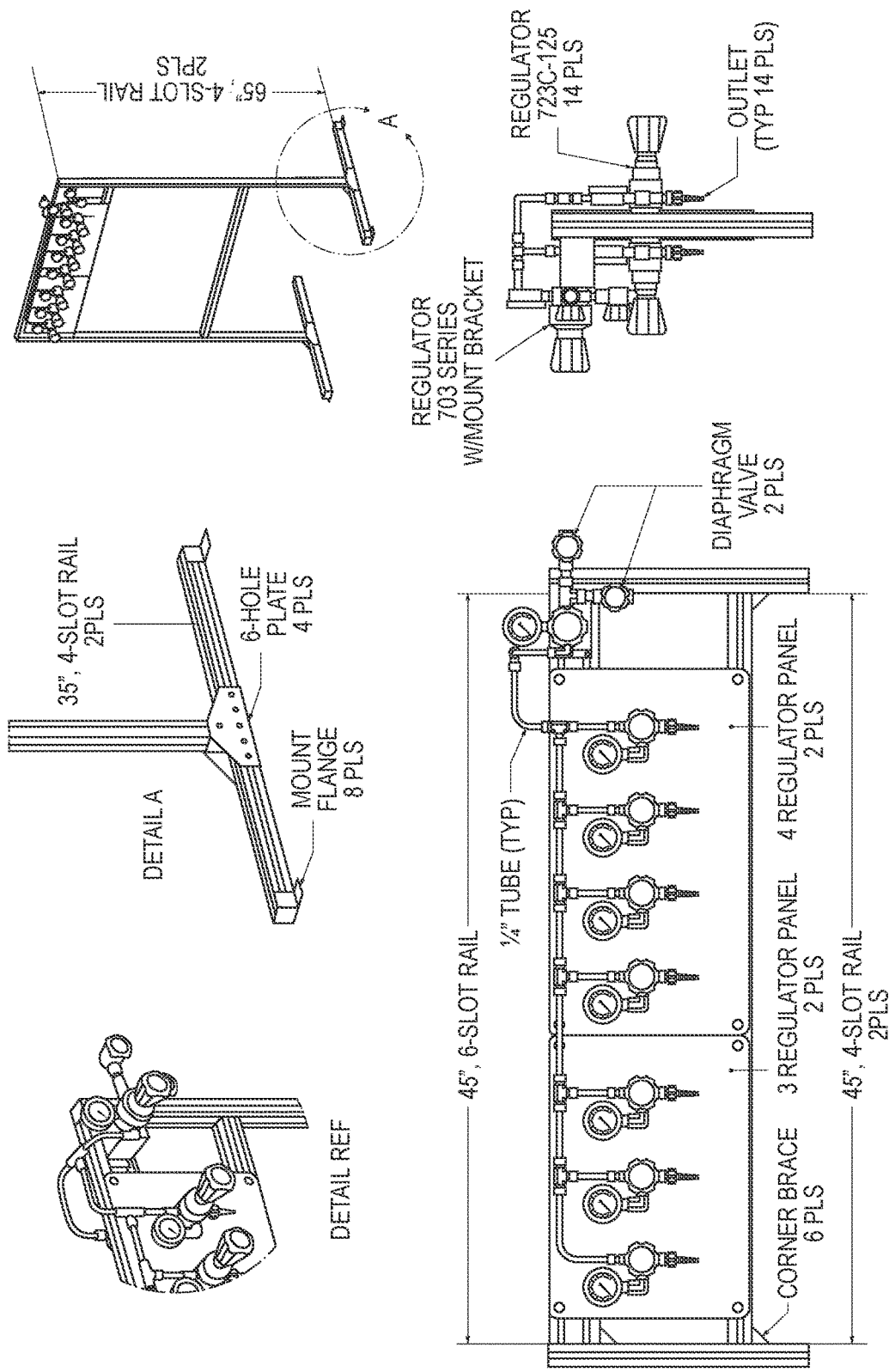
FIG. 6 illustrates several views of several portions of a mobile oxygen point of use apparatus configured with 15 liters per minute (LPM) regulators for cannulas/breathing masks.

FIG. 6 illustrates several views of several portions of a mobile oxygen point of use apparatus 600 configured with 15 LPM regulators for cannulas or breathing masks. Cannulas and breathing masks are well known in the art. FIG. 6 shows various features including slot rails, mount flanges, hole plates, mount brackets, corner braces, diaphragm valves, regulators, outlets, and regulator panels. For example, a diaphragm valve has a body with at least two ports, an elastomeric diaphragm, and a weir or saddle or seat upon which the valve is closed by the diaphragm.

Figure 7:
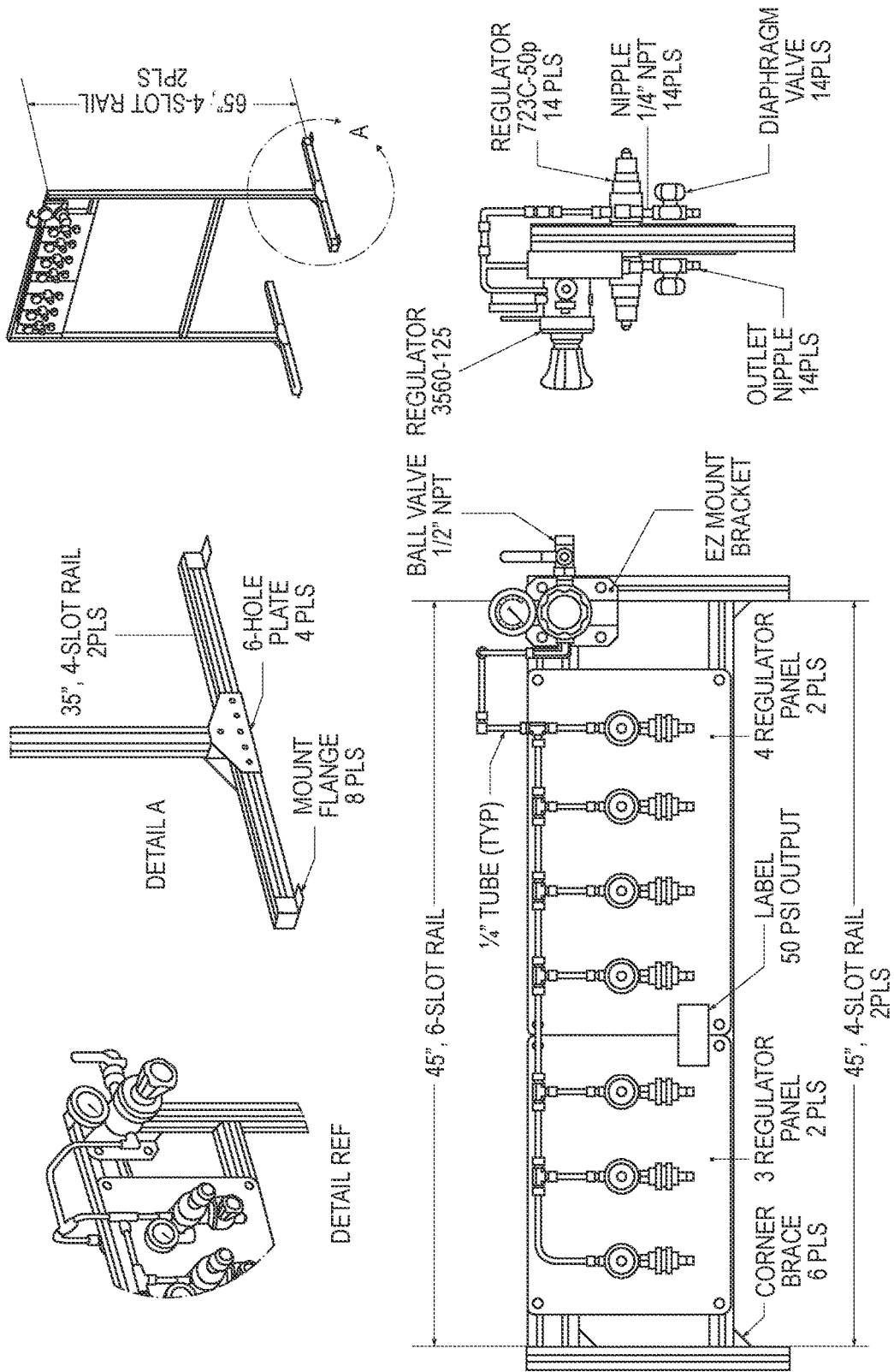
FIG. 7 illustrates several views of several portions of a mobile oxygen point of use apparatus configured with 50 pounds per square inch (PSI) preset regulators for respirators/ventilators.

FIG. 7 illustrates several views of several portions of a mobile oxygen point of use apparatus 700 configured with 50 PSI preset regulators for respirators or ventilators. Respirators and ventilators are well known in the art. FIG. 7 shows various features including slot rails, mount flanges, hole plates, mount brackets, corner braces, diaphragm valves, regulators, a ball valve, outlet nipples, a label, and regulator panels. For example, a ball valve uses a pivoting ball and is closed when the ball is lined up, via a handle, to block the flow. The ball valve is open when the ball is pivoted away from the flow via the handle.

While the disclosed embodiments have been illustrated and described in considerable detail, it is not the intention to restrict or in any way limit the scope of the appended claims to such detail. It is, of course, not possible to describe every conceivable combination of components or methodologies for purposes of describing the various aspects of the subject matter. Therefore, the disclosure is not limited to the specific details or illustrative examples shown and described. Thus, this disclosure is intended to embrace alterations, modifications, and variations that fall within the scope of the appended claims, which satisfy the statutory subject matter requirements of 35 U.S.C. § 101. The above description of specific embodiments has been given by way of example. From the disclosure given, those skilled in the art will not only understand the general inventive concepts and attendant advantages, but will also find apparent various changes and modifications to the structures and methods disclosed. It is sought, therefore, to cover all such changes and modifications as fall within the spirit and scope of the general inventive concepts, as defined by the appended claims, and equivalents thereof.

What is claimed is:

1. A mobile oxygen point of use apparatus, comprising:
   a standalone and portable mounting panel having a first side and a second side and configured to be portably relocated within a facility by at least one human operator;
   a first set of oxygen flow regulators mounted on the first side of the mounting panel having a first plurality of oxygen inputs and a first plurality of oxygen outputs;
   a second set of oxygen flow regulators mounted on the second side of the mounting panel having a second plurality of oxygen inputs and a second plurality of oxygen outputs;
   a low pressure oxygen input mounted on the mounting panel;
   a single pipeline or hose configured to be connected from the low pressure oxygen input to a source of oxygen;
   distribution plumbing connecting the low pressure oxygen input to the first plurality of oxygen inputs and the second plurality of oxygen inputs; and
   at least one of a frame or a stand connected to the mounting panel, wherein the frame or the stand is configured to support a plurality of oxygen tanks as the source of oxygen.

2. The mobile oxygen point of use apparatus of claim 1, wherein the frame or the stand includes feet.

3. The mobile oxygen point of use apparatus of claim 2, further comprising wheels connected to the feet of the frame or the stand.

4. The mobile oxygen point of use apparatus of claim 2, further comprising casters connected to the feet of the frame or the stand.

5. The mobile oxygen point of use apparatus of claim 2, further comprising rollers connected to the feet of the frame or the stand.

6. The mobile oxygen point of use apparatus of claim 1, wherein the first set of oxygen flow regulators and the second set of oxygen flow regulators are FDA Class 1 medical devices.

7. The mobile oxygen point of use apparatus of claim 1, wherein the first set of oxygen flow regulators and the second set of oxygen flow regulators are 15 LPM Class 1 regulators for use with cannulas or breathing masks.

8. The mobile oxygen point of use apparatus of claim 1, wherein the first set of oxygen flow regulators and the second set of oxygen flow regulators are 50 PSI preset Class 1 regulators for use with respirators and ventilators.

9. An oxygen distribution system, comprising:
   a mobile oxygen point of use apparatus, including:
      a standalone and portable mounting panel having a first side and a second side and configured to be portably relocated within a facility by at least one human operator;
      a first set of oxygen flow regulators mounted on the first side of the mounting panel having a first plurality of oxygen inputs and a first plurality of oxygen outputs;
      a second set of oxygen flow regulators mounted on the second side of the mounting panel having a second plurality of oxygen inputs and a second plurality of oxygen outputs;
      a low pressure oxygen input mounted on the mounting panel;
      a single pipeline or hose configured to be connected from the low pressure oxygen input to a source of oxygen;
      distribution plumbing connecting the low pressure oxygen input to the first plurality of oxygen inputs and the second plurality of oxygen inputs;
   and
   the source of oxygen configured to supply oxygen for use by the mobile oxygen point of use apparatus, wherein the source of oxygen includes a bulk tank oxygen storage system.

10. The oxygen distribution system of claim 9, wherein the first set of oxygen flow regulators and the second set of oxygen flow regulators of the mobile oxygen point of use apparatus are 15 LPM Class 1 regulators for use with cannulas or breathing masks.

11. The oxygen distribution system of claim 9, wherein the first set of oxygen flow regulators and the second set of oxygen flow regulators of the mobile oxygen point of use apparatus are 50 PSI preset Class 1 regulators for use with respirators and ventilators.

12. An oxygen distribution system, comprising:
a mobile oxygen point of use apparatus, including:
a standalone and portable mounting panel having a first side and a second side and configured to be portably relocated within a facility by at least one human operator,
a first set of oxygen flow regulators mounted on the first side of the mounting panel having a first plurality of oxygen inputs and a first plurality of oxygen outputs,
a second set of oxygen flow regulators mounted on the second side of the mounting panel having a second plurality of oxygen inputs and a second plurality of oxygen outputs,
a low pressure oxygen input mounted on the mounting panel,
a single pipeline or hose configured to be connected from the low pressure oxygen input to a source of oxygen, and
distribution plumbing connecting the low pressure oxygen input to the first plurality of oxygen inputs and the second plurality of oxygen inputs;
and
the source of oxygen configured to supply oxygen for use by the mobile oxygen point of use apparatus, wherein the source of oxygen includes a microbulk oxygen storage system.

13. An oxygen distribution system, comprising:
a mobile oxygen point of use apparatus, including:
a standalone and portable mounting panel having a first side and a second side and configured to be portably relocated within a facility by at least one human operator,
a first set of oxygen flow regulators mounted on the first side of the mounting panel having a first plurality of oxygen inputs and a first plurality of oxygen outputs,
a second set of oxygen flow regulators mounted on the second side of the mounting panel having a second plurality of oxygen inputs and a second plurality of oxygen outputs,
a low pressure oxygen input mounted on the mounting panel,
a single pipeline or hose configured to be connected from the low pressure oxygen input to a source of oxygen, and
distribution plumbing connecting the low pressure oxygen input to the first plurality of oxygen inputs and the second plurality of oxygen inputs;
and
the source of oxygen configured to supply oxygen for use by the mobile oxygen point of use apparatus, wherein the source of oxygen includes a liquid oxygen dewar storage system.

14. An oxygen distribution system, comprising:
a mobile oxygen point of use apparatus, including:
a standalone and portable mounting panel having a first side and a second side and configured to be portably relocated within a facility by at least one human operator,
a first set of oxygen flow regulators mounted on the first side of the mounting panel having a first plurality of oxygen inputs and a first plurality of oxygen outputs,
a second set of oxygen flow regulators mounted on the second side of the mounting panel having a second plurality of oxygen inputs and a second plurality of oxygen outputs,
a low pressure oxygen input mounted on the mounting panel,
a single pipeline or hose configured to be connected from the low pressure oxygen input to a source of oxygen, and
distribution plumbing connecting the low pressure oxygen input to the first plurality of oxygen inputs and the second plurality of oxygen inputs;
the source of oxygen configured to supply oxygen for use by the mobile oxygen point of use apparatus; and
a vaporizer configured between the source of oxygen and the mobile oxygen point of use apparatus to add moisture to the oxygen.

15. An oxygen distribution system, comprising:
a mobile oxygen point of use apparatus, including:
a standalone and portable mounting panel having a first side and a second side and configured to be portably relocated within a facility by at least one human operator,
a first set of oxygen flow regulators mounted on the first side of the mounting panel having a first plurality of oxygen inputs and a first plurality of oxygen outputs,
a second set of oxygen flow regulators mounted on the second side of the mounting panel having a second plurality of oxygen inputs and a second plurality of oxygen outputs,
a low pressure oxygen input mounted on the mounting panel,
a single pipeline or hose configured to be connected from the low pressure oxygen input to a source of oxygen, and
distribution plumbing connecting the low pressure oxygen input to the first plurality of oxygen inputs and the second plurality of oxygen inputs;
the source of oxygen configured to supply oxygen for use by the mobile oxygen point of use apparatus; and
a bulk manifold having multiple oxygen outputs and being configured between the source of oxygen and a plurality of the mobile oxygen point of use apparatus.

16. An oxygen distribution system, comprising:
a mobile oxygen point of use apparatus, including:
a standalone and portable mounting panel having a first side and a second side and configured to be portably relocated within a facility by at least one human operator,
a first set of oxygen flow regulators mounted on the first side of the mounting panel having a first plurality of oxygen inputs and a first plurality of oxygen outputs,
a second set of oxygen flow regulators mounted on the second side of the mounting panel having a second plurality of oxygen inputs and a second plurality of oxygen outputs,
a low pressure oxygen input mounted on the mounting panel,
a single pipeline or hose configured to be connected from the low pressure oxygen input to a source of oxygen, and
distribution plumbing connecting the low pressure oxygen input to the first plurality of oxygen inputs and the second plurality of oxygen inputs;

and
the source of oxygen configured to supply oxygen for use by the mobile oxygen point of use apparatus, wherein the source of oxygen includes a plurality of oxygen tanks, and wherein the mobile oxygen point of use apparatus further includes a frame or a stand configured to support the plurality of oxygen tanks.

\* \* \* \* \*